United States Patent
Horiike et al.

(10) Patent No.: US 10,585,073 B2
(45) Date of Patent: Mar. 10, 2020

(54) DISCHARGE IONIZATION CURRENT DETECTOR

(71) Applicant: SHIMADZU CORPORATION, Kyoto-shi, Kyoto (JP)

(72) Inventors: Shigeyoshi Horiike, Uji (JP); Kei Shinada, Uji (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 430 days.

(21) Appl. No.: 14/767,191

(22) PCT Filed: Feb. 15, 2013

(86) PCT No.: PCT/JP2013/053752
§ 371 (c)(1),
(2) Date: Aug. 11, 2015

(87) PCT Pub. No.: WO2014/125630
PCT Pub. Date: Aug. 21, 2014

(65) Prior Publication Data
US 2015/0377844 A1    Dec. 31, 2015

(51) Int. Cl.
*G01N 30/64*    (2006.01)
*G01N 27/70*    (2006.01)
*G01N 30/02*    (2006.01)

(52) U.S. Cl.
CPC .......... *G01N 30/64* (2013.01); *G01N 27/70* (2013.01); *G01N 2030/025* (2013.01); *G01N 2030/647* (2013.01)

(58) Field of Classification Search
CPC .. G01N 30/64; G01N 27/70; G01N 2030/025; G01N 2030/647
See application file for complete search history.

(56) References Cited

U.S. PATENT DOCUMENTS

| 2006/0208186 | A1 | 9/2006 | Goodley et al. |
| 2009/0090176 | A1* | 4/2009 | Toribio ................ G01N 33/241 73/152.18 |
| 2011/0316551 | A1* | 12/2011 | Shinada ................ G01N 30/64 324/464 |

FOREIGN PATENT DOCUMENTS

| EP | 1 703 541 A2 | 9/2006 |
| JP | 2006-261116 A | 9/2006 |
| JP | 2007-218843 A | 8/2007 |
| JP | 2007-315853 A | 12/2007 |

(Continued)

OTHER PUBLICATIONS

English Machine Translation of Hidetaka et al, JP 2007-315853 A, Dec. 6, 2007, Translated Jun. 2017.*

(Continued)

*Primary Examiner* — David Z Huang
(74) *Attorney, Agent, or Firm* — Sughrue Mion, PLLC

(57) ABSTRACT

A discharge ionization current detector of the present invention is used for a detector for a gas chromatograph and suitable for analyzing high-boiling components. A discharge ionization current detector 10 is mainly constituted by a plasma generating section 20 and an ion collecting section 30. Regarding the ion collecting section 30, an ion collecting electrode 31 and a bias electrode 32 are arranged, and furthermore, an insulating member made of sapphire or aluminum oxide having a purity equal to or greater than 99.5% is arranged between the ion collecting electrode 31 and the bias electrode 32.

2 Claims, 9 Drawing Sheets

(56) References Cited

FOREIGN PATENT DOCUMENTS

| JP | 2008-4673 A | 1/2008 |
|----|-------------|--------|
| JP | 2010-60354 | 3/2010 |
| JP | 2011-117854 A | 6/2011 |
| JP | 2011-158357 A | 8/2011 |
| JP | 2011-232071 A | 11/2011 |
| JP | 2012-8088 A | 1/2012 |
| JP | 2013-3070 A | 1/2013 |
| WO | 2012169419 A1 | 12/2012 |

OTHER PUBLICATIONS

Auerkari, "Mechanical and physical properties of engineering alumina ceramics", 1996, Vit Tiedotteita—Research Notes 1792, pp. 1-26.*
International Written Opinion for PCT/JP2013/053752 dated Mar. 19, 2013 [PCT/ISA/237].
International Search Report of PCT/JP2013/053659, dated Mar. 19, 2013. [PCT/ISA/210].
International Search Report for PCT/JP2013/053752 dated Mar. 19, 2013 [PCT/ISA/210].
International Written Opinion for PCT/JP2013/053659 dated Mar. 19, 2013. [PCT/ISA/237].

* cited by examiner

DISCHARGE IONIZATION CURRENT DETECTOR

CROSS REFERENCE TO RELATED APPLICATIONS

This application is a National Stage of International Application No. PCT/JP2013/053752, filed on Feb. 15, 2013, the contents of all of which are incorporated herein by reference in their entirety.

TECHNICAL FIELD

The present invention relates to a discharge ionization current detector primarily suitable as a detector for a gas chromatograph (GC), and more particularly relates to improvement in the characteristics of the detector at a high temperature.

BACKGROUND ART

As a detector for GC, the detectors of various types, such as a flame ionization detector (FID), a pulsed discharge detector (PDD), and a thermal conductivity detector (TCD), have been conventionally in practical use.

Among the aforementioned detectors, the FID is generally used in order to detect organic substances. The FID ionizes sample components in sample gas with hydrogen flames and detects a resultant ion current. The FID has the characteristic of a wide dynamic range, but compounds to be analyzed are limited because the sample is burned in the hydrogen flames to ionize the sample components. The FID has low sensitivity with respect to incombustible gas and no sensitivity with respect to inorganic gas.

In contrast, the PDD, in which the samples are ionized by use of electric discharge, has high sensitivity with respect to the incombustible gas or the inorganic gas, and is suitable for detecting almost all compounds with which the gas chromatograph is required to cope (for example, see Patent Literatures 1 to 4). The method of exciting helium molecules is often used for the generation of plasma, and the PDD in which this method is applied is referred to as a helium discharge photo ionization detector (HDPID).

The HDPID is mainly constituted by a plasma generating section and an ion collecting section.

A plasma excitation electrode is arranged in the plasma generating section. Helium gas is introduced into the plasma generating section, and a high voltage pulse is applied to the plasma excitation electrode, so that the helium gas is excited, thereby generating the plasma. The light (vacuum ultraviolet light and the like) emitted by the plasma reaches the ion collecting section.

An ion collecting electrode and a bias electrode are arranged in the ion collecting section. The sample gas is introduced into the ion collecting section, and the light reached from the plasma generating section is cast to the sample gas, thereby ionizing the sample gas (sample ions). Voltage is applied to the bias electrode, generating an electric field, and the sample ions are guided to the ion collecting electrode. The ion collecting electrode collects the sample ions and detects the sample ions as an ion current through an amplifier connected to the ion collecting electrode.

An insulating member of, for example, ceramic (having thickness of several millimeters) is inserted between the ion collecting electrode and the bias electrode to electrically insulate one from the other (for example, see Patent Literatures 1 to 4).

CITATION LIST

Patent Literature

Patent Literature 1: JP 2011-117854 A
Patent Literature 2: JP 2011-158357 A
Patent Literature 3: JP 2011-232071 A
Patent Literature 4: JP 2012-8088 A

SUMMARY OF INVENTION

Technical Problem

Regarding the gas chromatograph, high-boiling-point components are sometimes analyzed, in which case it is necessary to heat the ion collecting section of the HDPID up to about 400 degrees Celsius, in order to facilitate the ionization of the components. However, when the ion collecting section is thus heated, temperature drift or noise abruptly grows at above 300 degrees Celsius, and as a result, a background level increases, and the signal-to-noise (S/N) ratio of the detection signal deteriorates.

The present invention has been achieved to solve the above-mentioned problems. It is an object of the present invention to provide a discharge ionization current detector that prevents the deterioration of the S/N ratio of the detection signal at high temperatures, and is suitable for analyzing high-boiling-point components.

Solution to Problem

One aspect of the present invention that has been achieved in order to solve the above-mentioned problems is a discharge ionization current detector used for a gas chromatograph which includes:

a) a plasma generating section configured to generate plasma, and b) an ion collecting section including: a bias electrode configured to generate an electric field that guides sample ions, which are ionized by light emitted by the plasma generated by the plasma generating section, to a later-described ion collecting electrode; the ion collecting electrode configured to collect the sample ions; and an insulating member arranged between the ion collecting electrode and the bias electrode and made of sapphire or aluminum oxide having a purity equal to or larger than 99.5%.

The inventors of the present application have found that, when the ion collecting section is heated, the electric resistance of the insulating member abruptly lowers at a temperature equal to or higher than 300 degrees Celsius, and this is the primary cause of deterioration of the S/N ratio of the detection signal. That is, conventionally used insulating members such as aluminum oxide and heat-resistant resin have electric resistance significantly lowering at a temperature equal to or higher than 300 degrees Celsius, and as a result, the isolation between the bias electrode and the ion collecting electrode is inadequately assured, causing electrical current flow from the bias electrode to the ion collecting electrode, which is detected as the drift or noise.

As the result of further examination given based on these findings, it has been found that the electric resistance of the insulating member is prevented from rapidly lowering at a temperature equal to or higher than 300 degrees Celsius, by using sapphire or aluminum oxide having a purity equal to or larger than 99.5% as the insulating members between the ion collecting electrode and the bias electrode. These insulating members have the volume resistivity of the order of $10^{10}$ Ωcm or more even at the maximum operating temperature (approximately 400 degrees Celsius) of the detector and achieve adequate isolation between the bias electrode and the ion collecting electrode.

Furthermore, regarding the discharge ionization current detector, the plasma generating section can be configured to generate the plasma by utilizing dielectric barrier discharge of a low-frequency alternating-current electric field.

The inventors of the present invention have identified that the generation of gas discharged from the inner wall of the detector inclusive of the plasma generating section due to the heat of the ion collecting section is one of the leading causes of deterioration of the S/N ratio of the detection signal. The gas discharged is mainly composed of inorganic gas such as hydrogen and oxygen, and as described above, the detector, in which the electric discharge is utilized, detects the inorganic gas with high sensitivity, so that the gas discharged is unnecessarily detected. Accordingly, the background level increases, and the S/N ratio of the detection signal deteriorates.

The discharge ionization current detector including the plasma generating means having the aforementioned constitution is generally referred to as a low-frequency dielectric barrier discharge ionization detector (BID). Regarding the BID, a space surrounded by a dielectric substance is provided in the plasma generating section, and a plasma excitation electrode is arranged on the outside of the dielectric substance, thereby generating plasma in the space. Accordingly, this suppresses the sputtering of the electrode or the generation of gas discharged, which is attributed to the direct exposure of the plasma and the like to the aforementioned electrode and the inner wall of the detector.

The amount of gas discharged, which is generated from the inner wall of the detector, can be greatly reduced even at a high temperature, through the use of this dielectric barrier discharge.

Also, it can be configured such that each metallic O-ring is arranged between the ion collecting electrode, the insulating member, and the bias electrode, which are pressed by an elastic member and fixed.

The metallic O-ring may be made of a nickel base superalloy to which gold plating or silver plating is applied.

A plate spring can be used as the elastic member, for example.

Conventionally, gaskets are arranged on the contact surfaces of the ion collecting electrode, the insulating member, and the bias electrode, thereby maintaining the airtightness of the ion collecting section. However, when the detector subjected to high temperatures is continuously used for a long period of time, the gaskets suffer plastic deformation due to temperature cycles, and the airtightness of the ion collecting section deteriorates. As a result, the inorganic gas may intrude through the contact surface into the ion collecting section, and the S/N ratio of the detection signal lowers.

In contrast, the metallic O-ring excels in shape restoring ability and hardly suffers plastic deformation due to temperature cycles even when the detector is continuously used for a long period of time, so that the airtightness of the ion collecting section can be maintained.

Alternatively, it can be configured such that the ion collecting electrode, the insulating member, and the bias electrode are airtightly joined with joining members.

In this case, it may be such that, on the insulating member, a first joining surface that joins the ion collecting electrode, and a second joining surface that joins the bias electrode are plated with nickel (Ni) on which molybdenum (Mo) and manganese (Mn) are metallized, and the insulating member and the ion collecting electrode are brazed on the first joining surface, and the insulating member and the bias electrode are brazed on the second joining surface.

Furthermore, a part of the brazing material used for the first joining surface and the second joining surface and exposed to the outside of the ion collecting section may be plated with nickel (Ni).

The ion collecting electrode and the bias electrode, for example, may be electrodes formed of stainless steel or nickel in such a manner that a passive state is formed on the surface thereof, so that oxidation can be prevented, but herein, in particular, it is desirable that the ion collecting electrode and the bias electrode be formed of an alloy made of iron, nickel, and cobalt.

This alloy can prevent the oxidation by being plated with nickel (Ni).

As described above, the ion collecting electrode, the insulating member, and the bias electrode are joined, thereby securing the airtightness of the ion collecting section. In particular, the thermal expansion coefficient of the alloy made of iron, nickel, and cobalt is close to the thermal expansion coefficient of aluminum oxide or sapphire, and the ion collecting electrode and the bias electrode are provided as electrodes made of the aforementioned alloy, so that the ion collecting electrode and the bias electrode can be resistant to the temperature cycles in the long term use of the detector.

The joining surfaces of the ion collecting electrode, the insulating member, and the bias electrode are exposed to the air on the outside of the ion collecting section. Accordingly, the brazing materials exposed from the joining surfaces may be oxidized and get swollen at a high temperature, which deteriorates the airtightness. However, as described above, the brazing materials exposed to the outside of the ion collecting section are plated with nickel (Ni), which serve as a barrier layers, so that oxidation can be prevented.

It is noted that the ion collecting electrode is connected to the amplifier or the like disposed outside of the ion collecting section, so that the ion collecting electrode is also exposed to the air. In this case, when the ion collecting section is heated, the ion collecting electrode may be oxidized in the connection portion. The discharge ionization current detector detects ion current of as low as a few picoamperes flowing through the ion collecting electrode. Accordingly, if the ion collecting electrode is oxidized, and even a slight contact failure or the like occurs between the ion collecting electrode and the amplifier or the like, the sensitivity of the detector is greatly reduced. Moreover, the bias electrode is connected to the power source or the like disposed outside of the ion collecting section, so that the bias electrode is exposed to the air. The oxidation of the bias electrode causes noise. The bias electrode is preferentially prone to be oxidized due to anodic oxidation. In this case, both electrodes may be plated with nickel (Ni) thereby to prevent the oxidation.

Also, the ion collecting electrode and/or the bias electrode may be formed by a conductive surface for which part of the insulating member is plated with a conductor, and a conductive pin that penetrates the insulating member and is electrically connected to the conductive surface.

The ion collecting electrode and/or the bias electrode is formed in the aforementioned manner, so that the air can be prevented from intruding into the ion collecting section through the contact surfaces between the aforementioned electrodes and the insulating members.

Regarding the discharge ionization current detector, it is desirable that the dead space of the ion collecting section be minimized in order not to waste the sample ions. Accordingly, regarding the aforementioned discharge ionization current detector, it is desirably configured such that the ion collecting electrode, the insulating member, and the bias electrode are formed in a cylindrical shape having holes whose diameters are identical, and the holes are provided in respective centers thereof, and the ion collecting electrode, the insulating member, and the bias electrode are arranged by making the holes coincide with each other so as to form a through hole, and the sample ions are confined in the through hole.

Advantageous Effects of the Invention

According to the discharge ionization current detector of the present invention, the deterioration of the S/N ratio of a detection signal at a high temperature can be prevented, and the favorable results of measurements in terms of analysis on high-boiling-point components can be obtained.

BRIEF DESCRIPTION OF DRAWINGS

FIG. 9A illustrates a case where the setting temperature of the ion collecting section is 200 degrees Celsius, and FIG. 9B illustrates a case where the setting temperature of the ion collecting section is 450 degrees Celsius.

FIG. 10A illustrates a case where the setting temperature of the ion collecting section is 200 degrees Celsius, and FIG. 10B illustrates a case where the setting temperature of the ion collecting section is 450 degrees Celsius.

DESCRIPTION OF EMBODIMENTS

Hereinafter, an embodiment of the present invention will be described referring to drawings.

Figure 1:
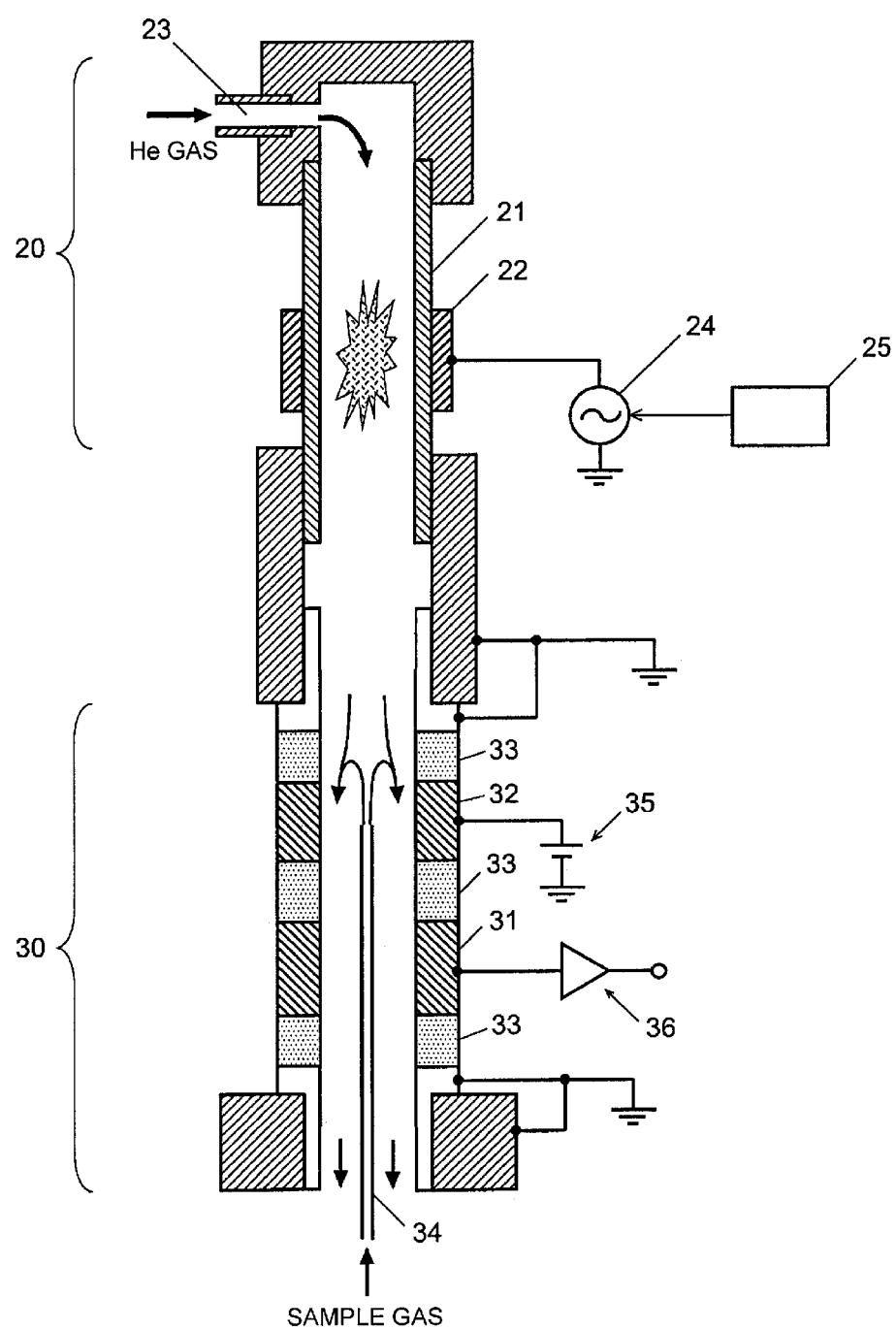
FIG. 1 is a view illustrating the schematic configuration of a discharge ionization current detector of a first embodiment of the present invention.

FIG. 1 is a schematic configuration view of a discharge ionization current detector of a first embodiment of the present invention and illustrates the cross section of a discharge ionization current detector 10 formed in a cylindrical shape. The discharge ionization current detector 10 is mainly constituted of a plasma generating section 20 and an ion collecting section 30.

A gas introduction port 23 is provided above the plasma generating section 20, and a cylindrical pipe 21 made of a dielectric substance such as synthetic quartz is provided below the gas introduction port 23. A plasma generating electrode 22 is arranged on the outer side of the cylindrical pipe 21, and a low-frequency alternating-current power supply 24 is connected to the electrode 22. The alternating-current power supply 24 is provided in such a manner as to be capable of controlling voltages and frequencies by means of a controller 25.

Regarding the ion collecting section 30, an insulating member 33, a bias electrode 32, the insulating member 33, an ion collecting electrode 31, and the insulating member 33 are provided in the order from the top thereof. With this arrangement, the ion collecting electrode 31 and the bias electrode 32 are insulated, and furthermore, both electrodes are insulated from a ground potential. It is preferable that the ion collecting electrode 31 and the bias electrode 32 be formed of stainless steel or nickel to prevent oxidation.

Regarding the insulating member 33, for example, aluminum oxide or sapphire having a purity equal to or larger than 99.5% is used, and the thickness thereof is approximately 1 to 4 mm, preferably, approximately 1.5 mm. Furthermore, a capillary 34 for introducing sample gas is inserted from below of the discharge ionization current detector 10 and fixed in such a manner that the tip end of the capillary 34 is positioned in the vicinity of the center of the bias electrode 32. The ion collecting electrode 31 is connected to an external circuit (not illustrated) via an amplifier 36, and the bias electrode 32 is connected to a direct-current power source 35. Moreover, the ion collecting section 30 is provided in such a manner that the temperature thereof can be adjusted by a heat source (not illustrated) such as a heater, approximately up to 450 degrees Celsius, for analyzing the sample of a high-boiling-point component.

Hereinafter, the operation of the discharge ionization current detector 10 will be described. In the plasma generating section 20, helium gas is introduced from the gas introduction port 23 into the interior thereof. Also, the alternating-current power supply 24 is controlled by the controller 25, and a low-frequency alternating-current voltage, whose frequency ranges approximately 5 to 50 kHz, and whose voltage ranges approximately 4 to 8 kVp-p, is applied to the plasma generating electrode 22, thereby generating electric discharge. The electric discharge is dielectric barrier discharge where the cylindrical pipe 21 serves as a dielectric substance and this excites the helium gas to generate helium plasma. The helium plasma emits light (mainly, vacuum ultraviolet light), and the light reaches the ion collecting section 30.

In contrast, the ion collecting section 30 is provided such that, while the external circuit inclusive of the amplifier 36 is operated, the ions collected by the ion collecting electrode 31 can be detected as an ion current. Also, voltage is applied to the bias electrode 32 by means of the direct-current power source 35. The voltage is a direct-current voltage ranging from approximately +50 to 200 V, preferably, approximately +170 V in terms of the linearity of signal response. In this state, the sample gas is introduced by the capillary 34.

The sample gas introduced is blown out upward from the tip end of the capillary 34. Here, the vacuum ultraviolet light generated in the plasma generating section 20 is emitted to the sample gas. Accordingly, the sample gas is ionized and turned into sample ions. The sample ions are influenced by the electric field formed by the voltage applied to the bias electrode 32 and guided to the ion collecting electrode 31 positioned below. The sample ions reached the ion collecting electrode 31 are detected as the ion current through the amplifier 36.

In this way, the sample component can be ionized and detected. In the first embodiment, sapphire or aluminum oxide having a purity equal to or larger than 99.5% is used for the insulating member 33, so that excellent effects can be obtained. Hereinafter, the effects will be described referring to FIGS. 6 to 10.

Figure 6:
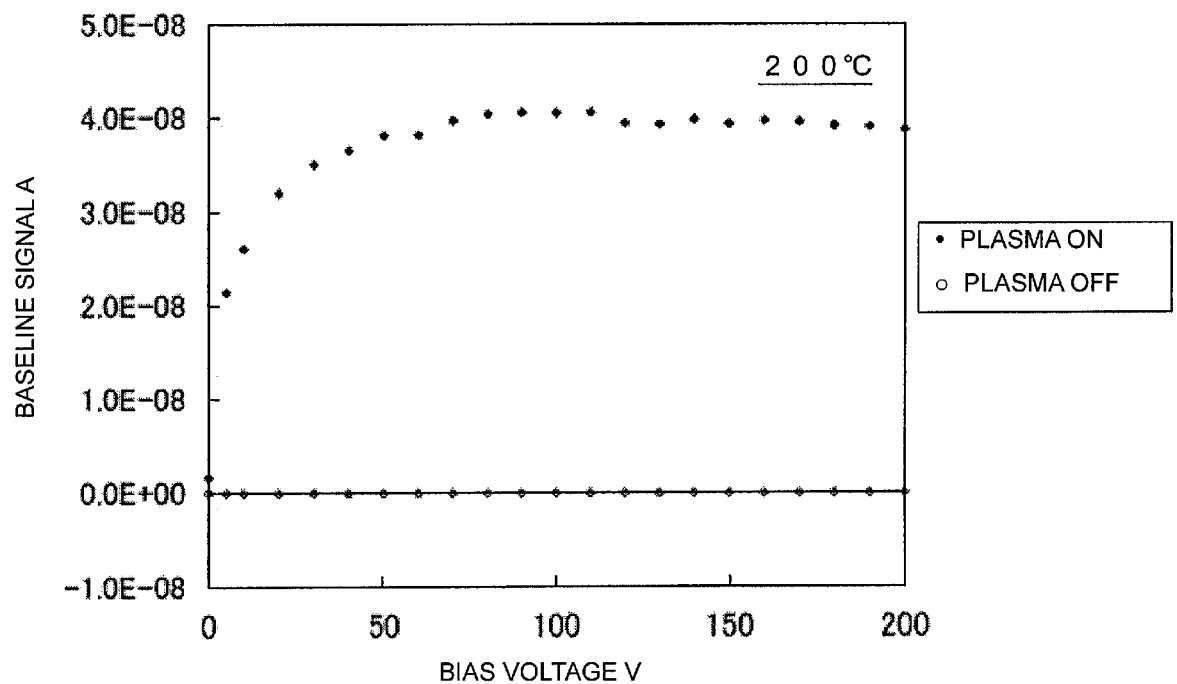
FIG. 6 is a graph illustrating the relation (IV characteristic) of the voltage of a bias electrode and the ion current obtained by an ion collecting electrode in a conventional discharge ionization current detector in which aluminum oxide having a purity less than 99.5% is used for an insulating member. The setting temperature of the ion collecting section is 200 degrees Celsius.
Figure 7:
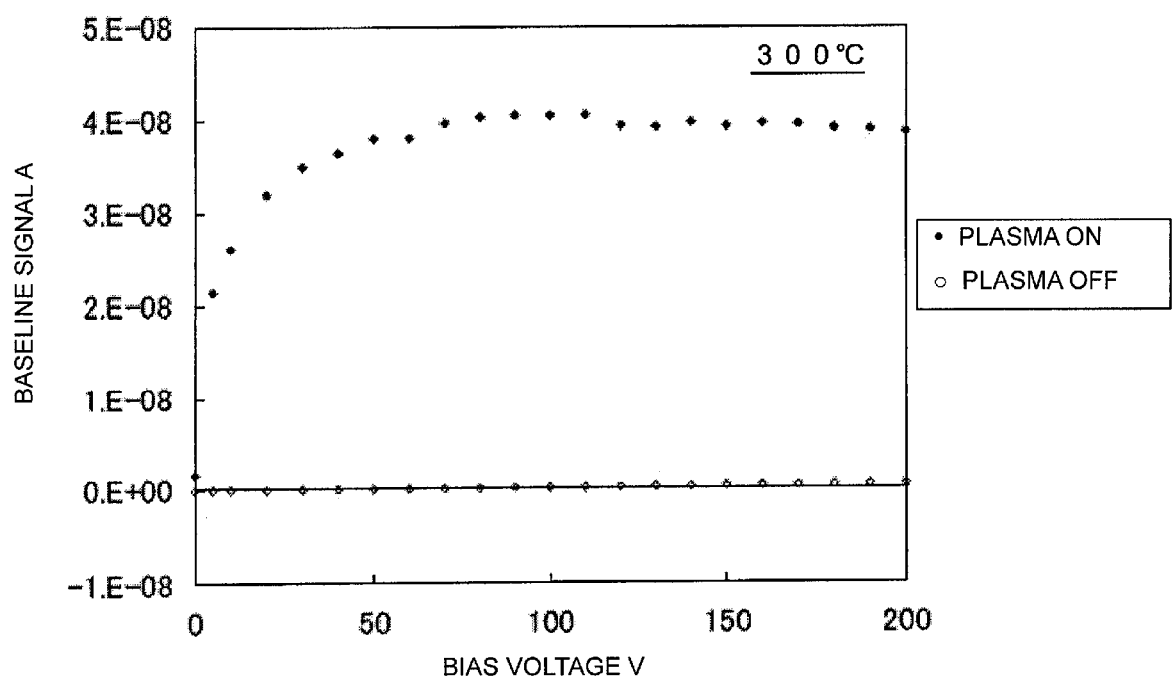
FIG. 7 is a graph illustrating the relation (IV characteristic) of the voltage of the bias electrode and the ion current obtained by the ion collecting electrode in the conventional discharge ionization current detector in which the aluminum oxide having a purity less than 99.5% is used for the insulating member. The setting temperature of the ion collecting section is 300 degrees Celsius.
Figure 8:
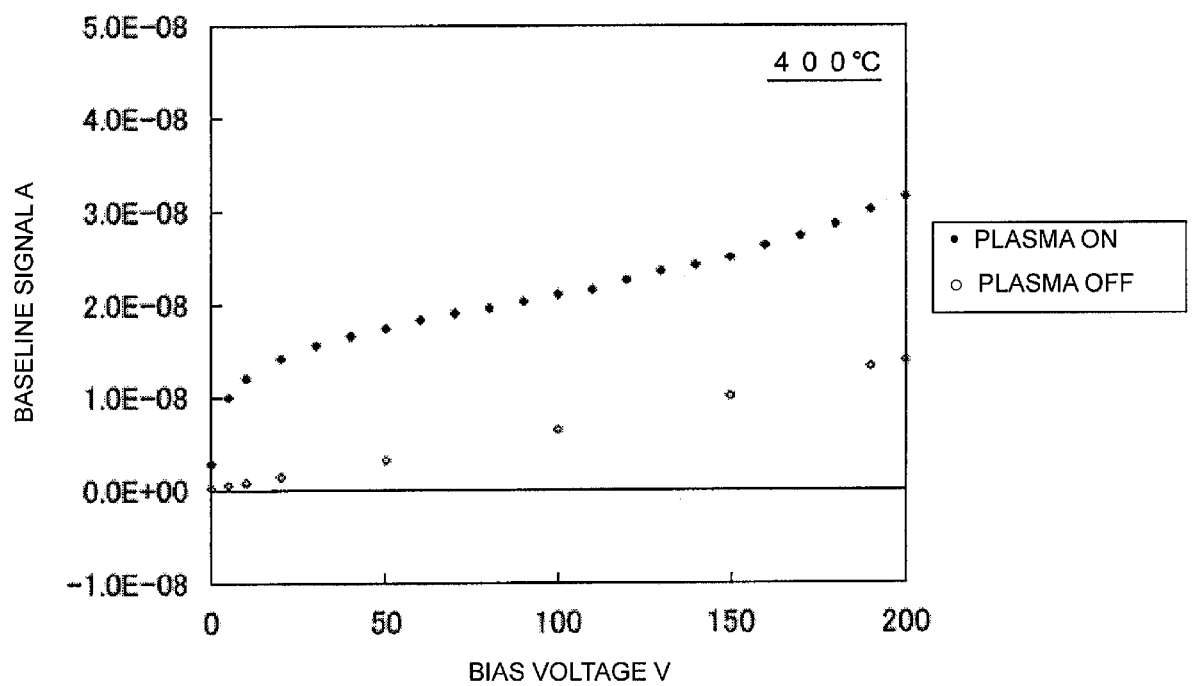
FIG. 8 is a graph illustrating the relation (IV characteristic) of the voltage of the bias electrode and the ion current obtained by the ion collecting electrode in the conventional discharge ionization current detector in which the aluminum oxide having a purity less than 99.5% is used for the insulating member. The setting temperature of the ion collecting section is 400 degrees Celsius.

Conventionally, for example, the aluminum oxide having a purity less than 99.5% has been used for the insulating member provided between the ion collecting electrode and the bias electrode. In this case, there is a problem in that the S/N ratio of a detection signal is deteriorated as the temperature of the ion collecting section increases. FIGS. 6 to 8 are graphs in which a bias voltage (V) applied to the bias electrode is plotted in the horizontal axis, and a baseline signal (A) as the ion current obtained by the ion collecting electrode is plotted in the vertical axis. Two types of plots are provided that respectively represent data in a case where the helium plasma is excited (plasma ON) and data in a case where the helium plasma is not excited (plasma OFF) in the plasma generating section. Three types of data are illustrated in FIGS. 6 to 8, which represent cases where the temperatures of the ion collecting section are set to 200, 300, and 400 degrees Celsius.

As a way of looking at the graphs, when the helium plasma is excited, it is desirable that the baseline signal remain substantially constant at the bias voltage (for example, equal to or higher than 50 V) during use of the detector, whereas when the helium plasma is not excited, it is preferable that the baseline signal keep nearly zero, irrespective of the bias voltage. It can be said that, when the temperature of the ion collecting section is set to 200 degrees Celsius, a desirable state is provided (see FIG. 6). In contrast, when the temperature of the ion collecting section is set to 300 degrees Celsius, it finds that the baseline signal increases as the bias voltage increases, even when the helium plasma is not excited (see FIG. 7). The fluctuation width of the baseline signal at this time is normally about 0.1 to 10 nA, and when the gas is discharged, the baseline signal exceeds 10 nA. Such a high baseline signal may cause background noise for the discharge ionization current detector that detects the minute ion current of approximately a few picoamperes.

Furthermore, when the temperature of the ion collecting section is set to 400 degrees Celsius, this tendency becomes noticeable, and when the helium plasma is not excited, the baseline signal drastically increases as the bias voltage increase. Even when the helium plasma is excited, the baseline signal does not remain constant in the range of the bias voltage equal to or higher than 100 V (FIG. 8).

The aforementioned matters mean that, when the temperature of the ion collecting section exceeds 300 degrees Celsius, the electric resistance is deteriorated in the case of using the conventional insulating member, which leads to the inadequate isolation between the ion collecting electrode and the bias electrode. Due to the inadequate isolation, the current flows from the bias electrode to the ion collecting electrode, which is detected as the drift or noise.

Figure 9A:
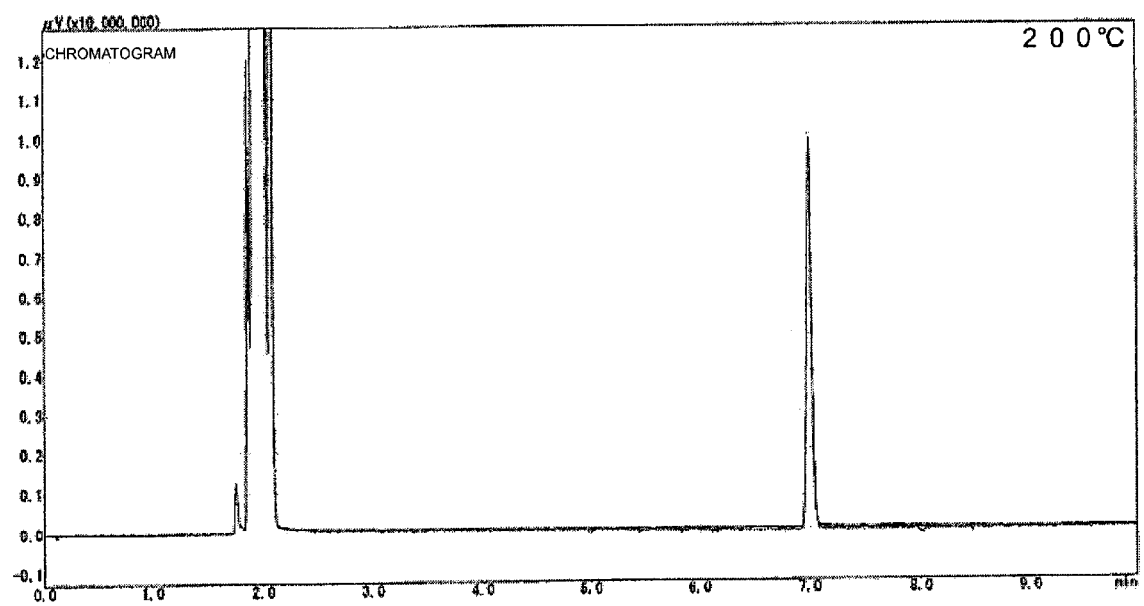
FIGS. 9A and 9B are graphs illustrating chromatograms of the conventional discharge ionization current detector in which the aluminum oxide having a purity less than 99.5% is used for the insulating member.
Figure 9B:
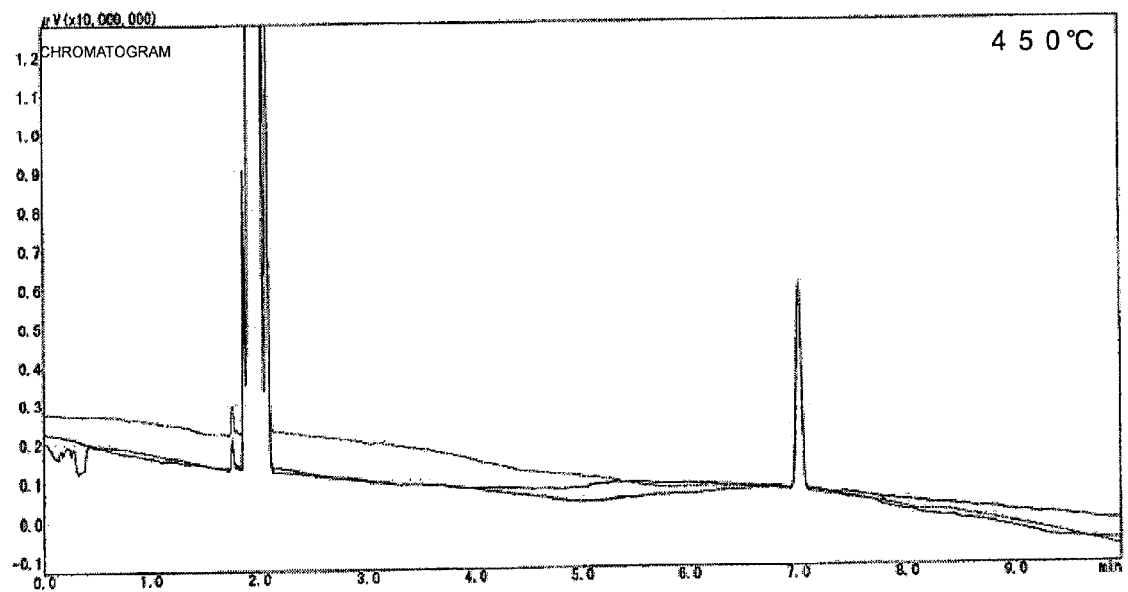

FIGS. 9A and 9B illustrate chromatograms, in which the horizontal axis represents time and the vertical axis represents detection intensity, which are obtained by the conventional discharge ionization current detector including the temperature characteristics of the aforementioned baseline signal. FIG. 9A illustrates a graph in a case where the temperature of the ion collecting section is set to 200 degrees Celsius, and FIG. 9B illustrates a graph in a case where the temperature of the ion collecting section is set to 450 degrees Celsius. Each graph is shown by superposing three chromatograms obtained by repeating the measurements of the same sample three times. When the setting temperature is 200 degrees Celsius, the three chromatograms are in a state of being almost overlapped (or coincident) with each other (FIG. 9A). In contrast, when the setting temperature is 450 degrees Celsius, the background noise increases, and the three chromatograms are different from each other (FIG. 9B). This fact shows that the S/N ratio of a detection signal and the precision of measurement are deteriorated as the temperature of the ion collecting section increases in the case of using the conventional discharge ionization current detector.

Figure 10A:
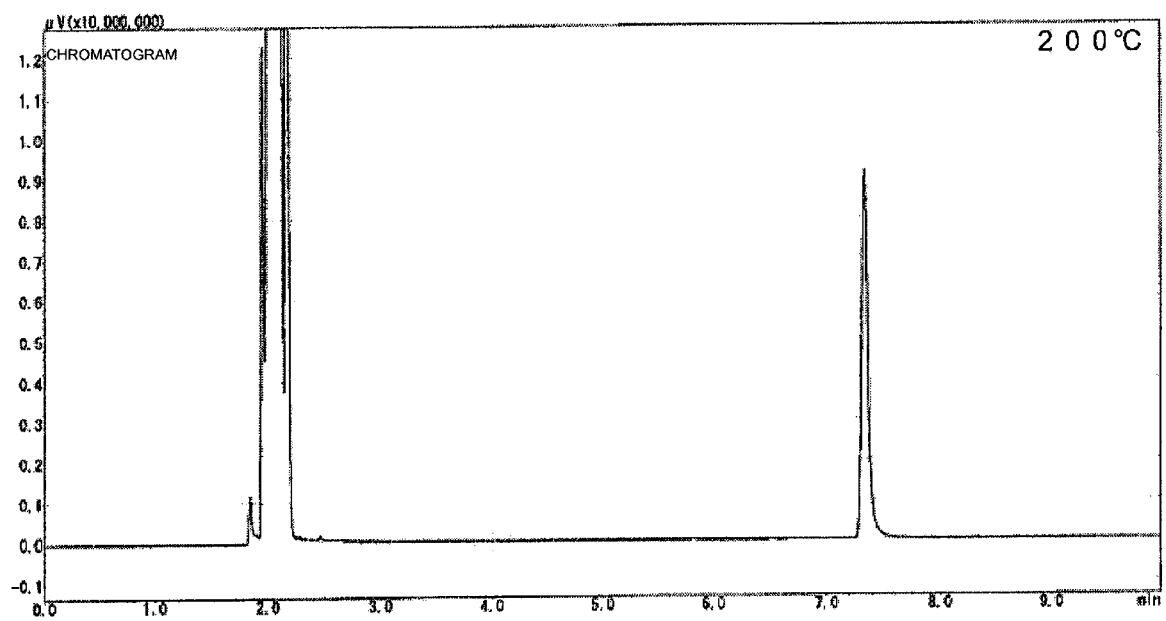
FIGS. 10A and 10B are graphs illustrating chromatograms of the discharge ionization current detector of the present invention, in which the aluminum oxide having a purity equal to or greater than 99.5% is used for the insulating member.
Figure 10B:
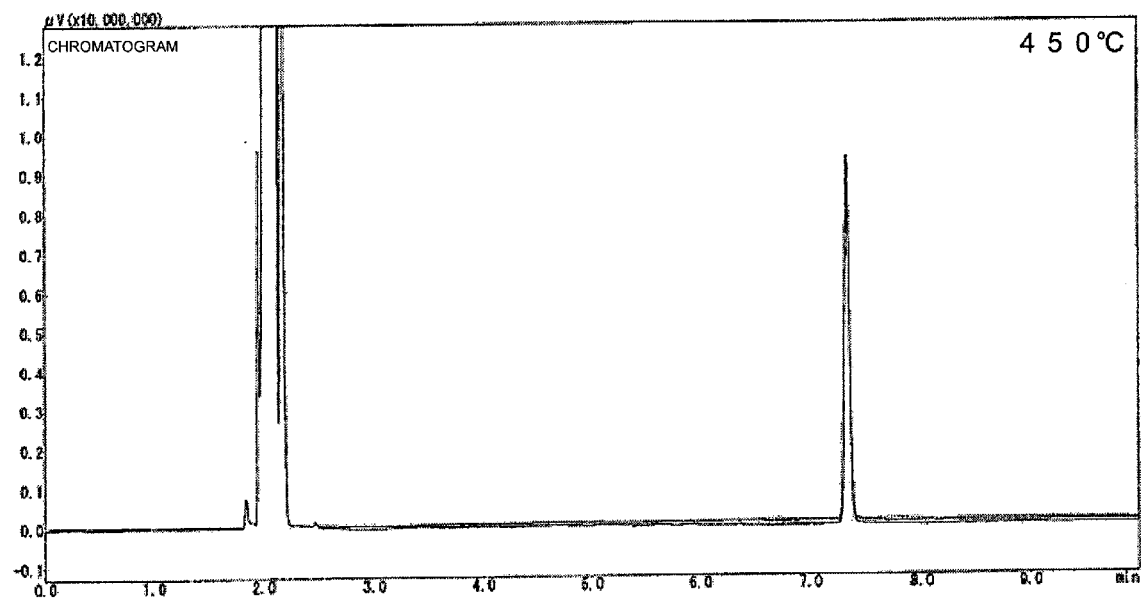

FIGS. 10A and 10B illustrate chromatograms obtained by the discharge ionization current detector of the first embodiment described above. In the discharge ionization current detector, even when the setting temperature is 450 degrees Celsius, the level of the background noise is the same as that of the case where the setting temperature is 200 degrees Celsius. Also, the three chromatograms are in a state of being almost overlapped (FIGS. 10A and 10B). That is, even when the temperature of the ion collecting section increases, the S/N ratio of a detection signal and the precision of measurement are not deteriorated. This is because, in the first embodiment, sapphire or aluminum oxide having a purity equal to or larger than 99.5% is used for the insulating member, which achieves adequate isolation between the ion collecting electrode and the bias electrode.

Even the aluminum oxide having a purity less than 99.5% (that is, conventional insulating member) achieves volumetric resistivity of around $10^{14}$ Ωcm in the vicinity of room temperatures but decreases the volumetric resistivity to around $10^8$ Ωcm at high temperatures from 300 to 500 degrees Celsius. In contrast, sapphire or aluminum oxide having a purity equal to or larger than 99.5% (that is, the insulating member of the aforementioned embodiment) achieves the specific volume resistance around $10^{10}$ Ωcm even at the high temperatures from 300 to 500 degrees Celsius. That is, a two-digit difference is found in the both specific volume resistance values at the high temperatures.

Hereinafter, the description will be given that the discharge ionization current detector of the present embodiment can improve performance by devising the arrangement structure of each electrode and the insulating member in the ion collecting section will be described.

Figure 2:
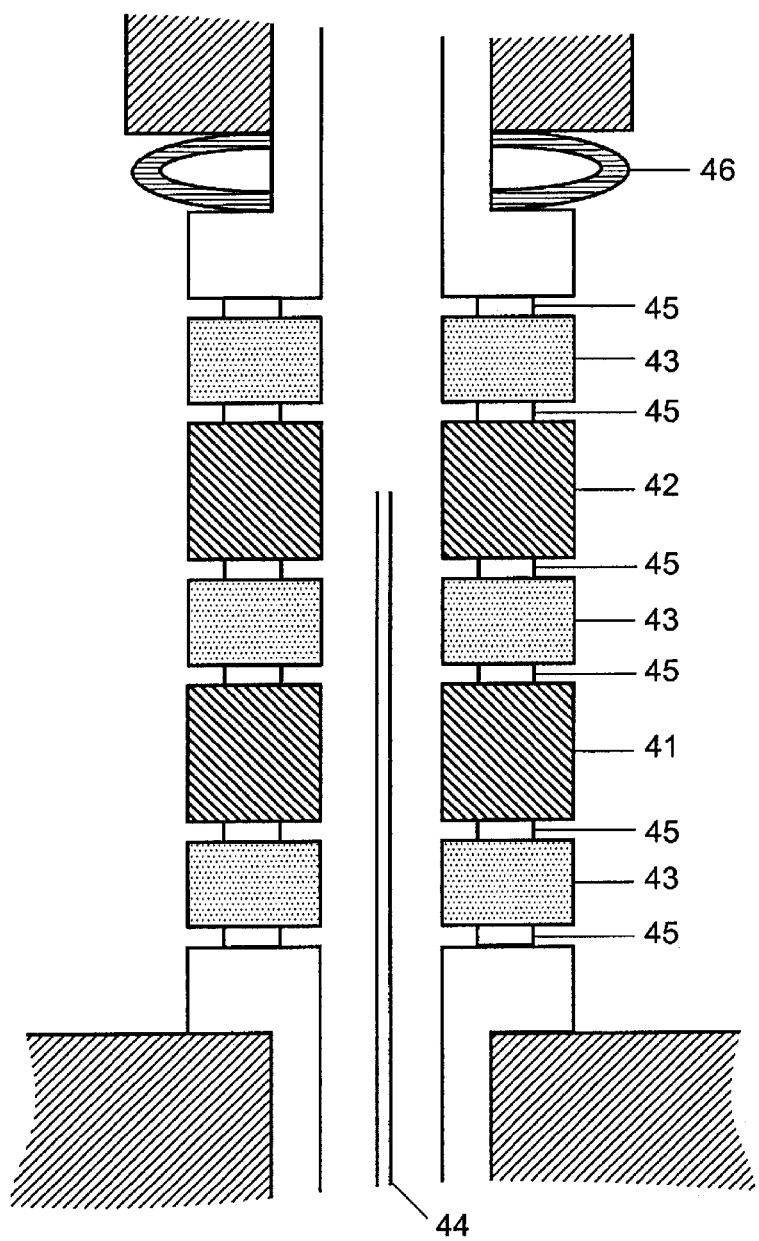
FIG. 2 is a view illustrating the schematic configuration of an ion collecting section of a conventional discharge ionization current detector.

First, FIG. 2 illustrates the schematic configuration of the ion collecting section of the conventional discharge ionization current detector. It is noted that the illustration of the amplifier connected to the ion collecting electrode, the direct-current power source connected to the bias electrode, and the like are omitted (the same is applied to FIGS. 3 and 4). In the conventional ion collecting section, gaskets 45 are arranged on the contact surfaces of an ion collecting electrode 41, insulating members 43, and a bias electrode 42, and airtightness is secured by pushing the gaskets 45 with a plate spring 46. With this constitution, the repetition of temperature cycles causes plastic deformation in the gaskets, which makes it impossible to maintain the airtightness. For this reason, for example, the air intrudes via the contact surfaces between the electrodes and the insulating members, and as a result, the S/N ratio of a detection signal is reduced.

Figure 3:
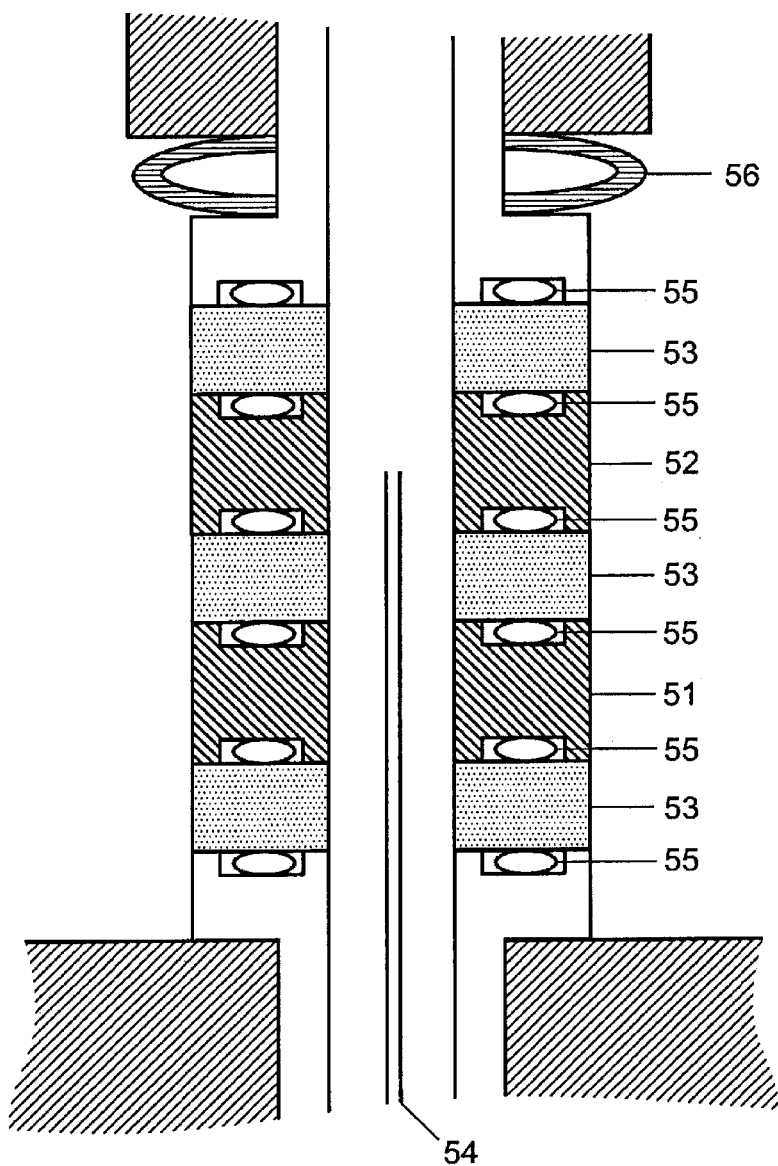
FIG. 3 is a view illustrating the schematic configuration of the ion collecting section of the discharge ionization current detector of a second embodiment of the present invention.

Hence, in the discharge ionization current detector of a second embodiment of the present invention, the ion collecting section may be constituted, for example, as illustrated in FIG. 3. With this constitution, metallic O-rings 55 are arranged on the contact surfaces of an ion collecting electrode 51, insulating members 53, and a bias electrode 52, and airtightness is secured by pushing the O-rings 55 with a plate spring 56. Inconel (registered trademark), for example, may be preferably used as a material of the metallic O-rings 55. The Inconel is a nickel base superalloy that excels in shape restoring ability at high temperatures, and use of the Inconel can prevent the plastic deformation of the O-rings due to the temperature cycles. Also, gold plating or silver plating may be applied to the surfaces of the O-rings, in order to prevent the oxidation of the O-rings 55.

Figure 4:
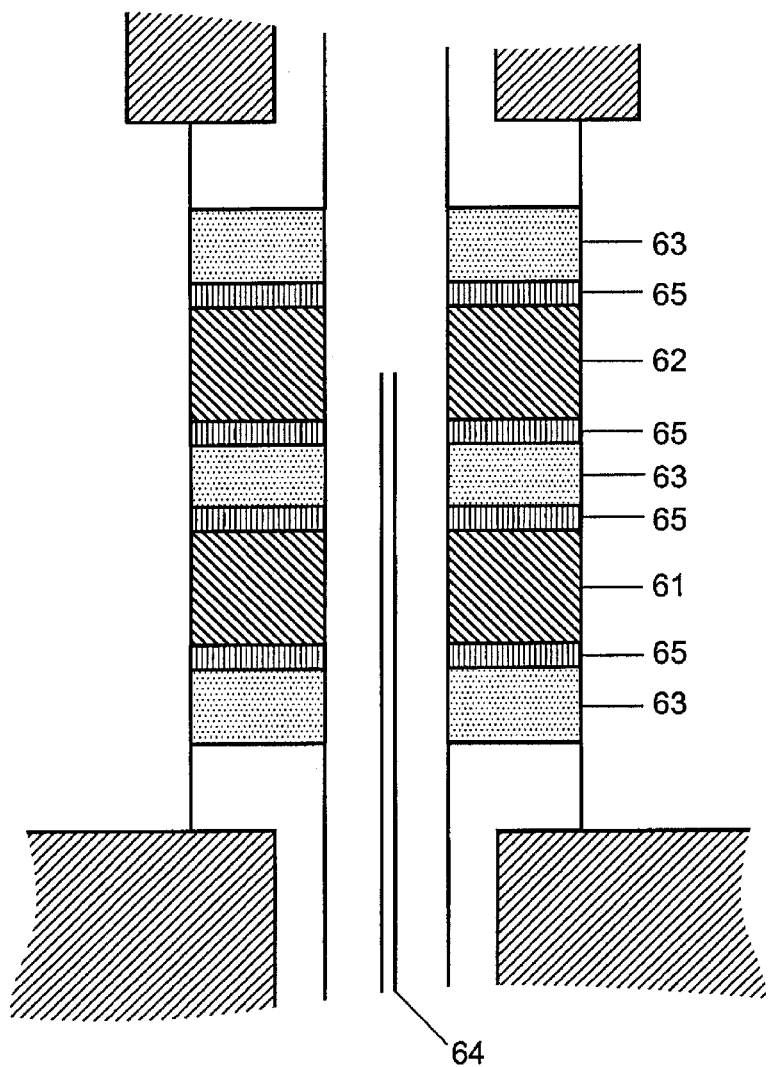
FIG. 4 is a view illustrating the schematic configuration of the ion collecting section of the discharge ionization current detector of a third embodiment of the present invention.

Alternatively, as another embodiment, the ion collecting section may be constituted as illustrated in FIG. 4 (third embodiment). With this constitution, an ion collecting electrode 61, insulating members 63, and a bias electrode 62 are joined by silver solder or other material (joining layers 65).

However, direct brazing in the insulating member 63 is impossible. Hence, the surfaces of the insulating members 63, on which the ion collecting electrode 61 and the bias electrode 62 are joined, may be plated in advance with nickel (Ni) on which molybdenum (Mo) and manganese (Mn) are metallized.

Also, for the ion collecting electrode and the bias electrode, an alloy made of iron, nickel, and cobalt, for which the coefficient of linear expansion is close to that of aluminum oxide or sapphire, may be employed. This alloy includes, for example, Kovar (registered trademark). Furthermore, the Kovar may be plated with nickel (Ni) in order to prevent oxidation.

Although not illustrated herein, as is the same with the ion collecting electrode 31 in FIG. 1, the ion collecting electrode 61 is connected to the external circuit through the amplifier and its connection portion is exposed to the air. Similarly, the brazing materials exposed from the joining surfaces of the insulating member 63 run the risk of oxidization due to the heat of the ion collecting section. Thus, the brazing materials exposed to the outside of the ion collecting section may also be plated with nickel (Ni).

Figure 5:
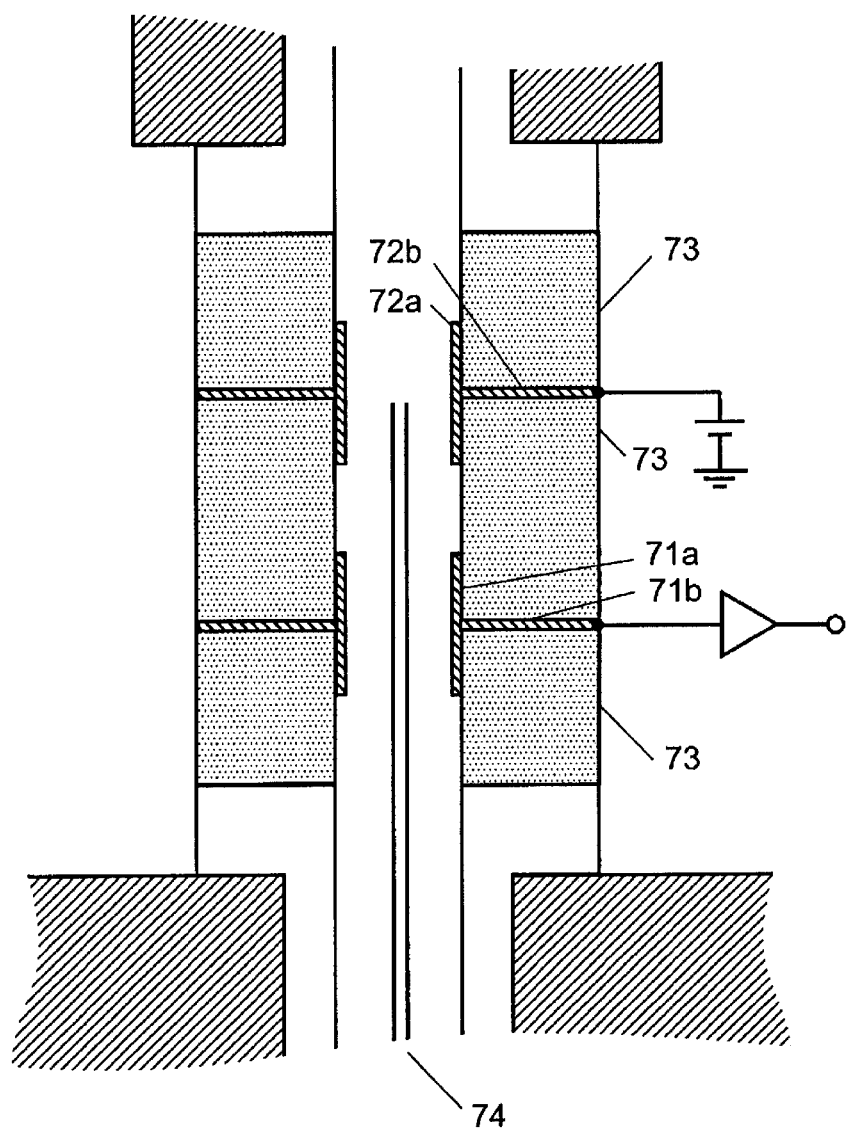
FIG. 5 is a view illustrating the schematic configuration of the ion collecting section of the discharge ionization current detector of a fourth embodiment of the present invention.

Moreover, the ion collecting section can be constituted as illustrated in FIG. 5 (fourth embodiment). With this constitution, the ion collecting electrode is formed by a conductive surface 71a for which part of an insulating member 73 is metallized and a conductive pin 71b that penetrates the insulating member 73. Similarly, the bias electrode is also formed by a conductive surface 72a for which part of the insulating member 73 is metallized and a conductive pin 72b that penetrates the insulating member 73. In this manner, the airtightness of the ion collecting section can be maintained.

It is noted that, in any of the aforementioned embodiments (the first to fourth embodiments), the same holes having the same diameter formed in a cylindrical shape are provided at the center of the ion collecting electrode, the bias electrode, and the insulating member of the ion collecting section, and the electrodes and the insulating member are stacked, thereby forming a through hole. With this arrangement, dead space in which the sample ions are wasted is reduced as much as possible.

REFERENCE SIGNS LIST

10 . . . Discharge ionization current detector
20 . . . Plasma generating section
21 . . . Cylindrical pipe
22 . . . Plasma generating electrode
23 . . . Gas introduction port
24 . . . Alternating-current power supply
30 . . . Ion collecting section
31, 41, 51, 61 . . . Ion collecting electrode
32, 42, 52, 62 . . . Bias electrode
33, 43, 53, 63, 73 . . . Insulating member
34, 44, 54, 64, 74 . . . Capillary
35 . . . Direct-current power source
36 . . . Amplifier
45 . . . Gasket
46, 56 . . . Plate spring
55 . . . O-ring
65 . . . Joining layer
71a . . . Conductive surface
71b . . . Conductive pin
72a . . . Conductive surface
72b . . . Conductive pin

The invention claimed is:

1. A discharge ionization current detector used for a gas chromatograph, comprising:

a) a plasma generator configured to generate plasma; and
b) an ion collecting section including:
a bias electrode configured to generate an electric field that guides sample ions, which are ionized by light emitted by the plasma generated by the plasma generator, to an ion collecting electrode;
the ion collecting electrode configured to collect the sample ions; and
an insulating member arranged between the ion collecting electrode and the bias electrode and made of aluminum oxide or sapphire having a purity equal to or larger than 99.5%;
wherein the ion collecting electrode, the insulating member, and the bias electrode are airtightly joined with a joining member,
wherein a first joining surface that joins the ion collecting electrode, and a second joining surface that joins the bias electrode of the insulating member are plated with nickel (Ni) on which molybdenum (Mo) and manganese (Mn) are metallized, and
wherein the insulating member and the ion collecting electrode are brazed on the first joining surface, and the insulating member and the bias electrode are brazed on the second joining surface.

2. The discharge ionization current detector according to claim 1,
   wherein on a joining portion of the ion collecting section, brazing materials exposed to an outside of the ion collecting section are also plated with the nickel (Ni).

* * * * *